(12) United States Patent
Gevgilili et al.

(10) Patent No.: US 11,642,303 B2
(45) Date of Patent: May 9, 2023

(54) HAIR CARE COMPOSITIONS COMPRISING CATIONIC COMPOUNDS, STARCH, AND SILANE COMPOUNDS

(71) Applicant: L'OREAL, Paris (FR)

(72) Inventors: Halil Gevgilili, Weehawken, NJ (US); Jun Liang, Staten Island, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/087,165

(22) Filed: Mar. 31, 2016

(65) Prior Publication Data
US 2017/0281522 A1  Oct. 5, 2017

(51) Int. Cl.
| | | |
|---|---|---|
| *A61Q 5/12* | (2006.01) | |
| *A61K 8/898* | (2006.01) | |
| *A61K 8/81* | (2006.01) | |
| *A61K 8/73* | (2006.01) | |
| *A61K 8/06* | (2006.01) | |
| *A61Q 5/02* | (2006.01) | |
| *A61K 8/34* | (2006.01) | |
| *A61K 8/49* | (2006.01) | |
| *A61K 8/41* | (2006.01) | |
| *A61K 8/58* | (2006.01) | |

(52) U.S. Cl.
CPC ............. *A61K 8/898* (2013.01); *A61K 8/068* (2013.01); *A61K 8/342* (2013.01); *A61K 8/416* (2013.01); *A61K 8/4946* (2013.01); *A61K 8/585* (2013.01); *A61K 8/732* (2013.01); *A61K 8/8152* (2013.01); *A61K 8/8176* (2013.01); *A61K 8/8182* (2013.01); *A61Q 5/02* (2013.01); *A61Q 5/12* (2013.01); *A61K 2800/262* (2013.01); *A61K 2800/5426* (2013.01); *A61K 2800/594* (2013.01); *A61K 2800/87* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 6,602,494 B1 | 8/2003 | Jahedshoar | |
| 7,030,985 B2 | 4/2006 | Jager Lezer | |
| 7,462,585 B2 | 12/2008 | Uehara | |
| 7,470,651 B2 | 12/2008 | Uehara | |
| 8,940,282 B2 | 1/2015 | Seng | |
| 2004/0131576 A1* | 7/2004 | Decoster | A61Q 19/10 424/70.122 |
| 2006/0286058 A1* | 12/2006 | Dhamdhere | A61K 8/8152 424/70.12 |
| 2006/0292104 A1 | 12/2006 | Saito | |
| 2007/0104671 A1* | 5/2007 | Fack | A61K 8/31 424/70.28 |
| 2012/0021025 A1 | 1/2012 | Leroy | |
| 2013/0034515 A1 | 2/2013 | Stone | |
| 2013/0164243 A1* | 6/2013 | Hoffman | A61K 8/37 424/70.9 |
| 2014/0076346 A1 | 3/2014 | Bourdin | |
| 2014/0196740 A1 | 7/2014 | Mette | |
| 2014/0246041 A1* | 9/2014 | Krueger | A61K 8/466 132/202 |

FOREIGN PATENT DOCUMENTS

| | | | |
|---|---|---|---|
| EP | 2347795 A2 | | 7/2011 |
| EP | 2623089 A2 | | 8/2013 |
| JP | 2014111574 A2 | | 6/2014 |
| JP | 2014201570 A2 | | 10/2014 |
| JP | 2014240380 A2 | | 12/2014 |
| JP | 2015074650 A2 | | 4/2015 |
| JP | 2015081255 A2 | | 4/2015 |
| JP | 2015086154 A2 | | 5/2015 |
| WO | WO 2012/163869 | * | 12/2012 |
| WO | 14177189 A1 | | 11/2014 |
| WO | 14177438 A1 | | 11/2014 |
| WO | 15013779 A1 | | 2/2015 |
| WO | 15013780 A1 | | 2/2015 |
| WO | 15188325 A1 | | 12/2015 |

OTHER PUBLICATIONS

SILSOFT 253, Marketing Bulletin (Aug. 2013).*

* cited by examiner

Primary Examiner — Jyothsna A Venkat
(74) Attorney, Agent, or Firm — The Marbury Law Group, PLLC

(57) ABSTRACT

Disclosed are compositions for treating and conditioning keratinous substrates, comprising a cationic agent comprising quaternary ammonium compounds; a modified starch; silane compounds, a cationic vinylpyrrolidone polymer and water. Also disclosed are methods treating and conditioning keratinous substrates using the composition.

14 Claims, 1 Drawing Sheet

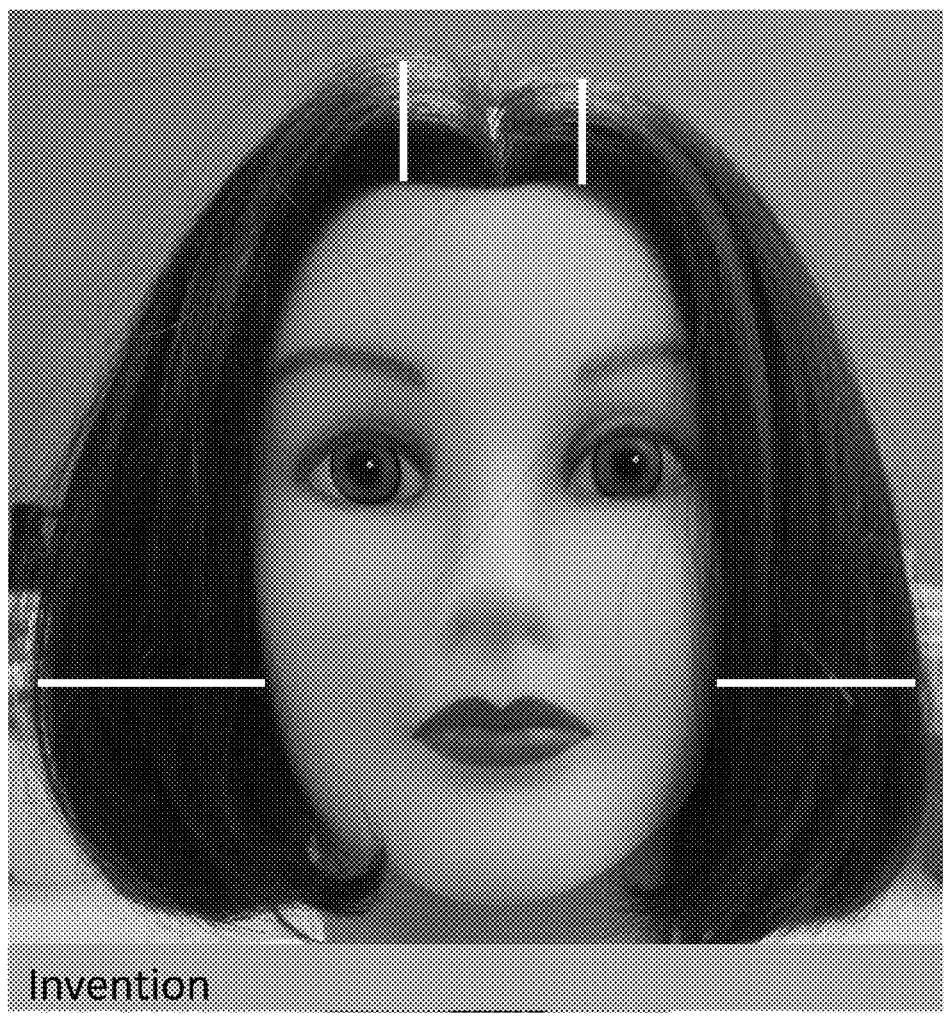

HAIR CARE COMPOSITIONS COMPRISING CATIONIC COMPOUNDS, STARCH, AND SILANE COMPOUNDS

FIELD OF THE INVENTION

The present application relates to cosmetic compositions for use on keratinous substrates, such as hair. In particular, it relates to compositions and methods for treating and conditioning hair.

BACKGROUND

Certain hair types are naturally thin and/or fine. In addition, any type of hair can diminish in quality and/or quantity over time by age and/or due to factors such as natural greasiness, sweat, shredded skin cells from the scalp, pollution, and dirt. These factors can result in thinning hair and/or harm the visual appearance and the feel of the hair, and lead to lank body and decreased volume. The magnitude of the consequences of these factors, which are almost all inevitable, is variable, depending on, for example, the quality of the hair, length, style, and environmental factors.

Hair care products are used to combat these drawbacks. Conventional cleansing compositions such as shampoos, for example, which contain surfactants such as anionic, nonionic and/or amphoteric type surfactants, can be employed to remove the diverse types of soils typically present on the substrate such as hair.

These cleansing compositions, while providing good cleansing power, may yield poor intrinsic cosmetic properties due to the fact that the nature of such a cleansing treatment may result in a less conditioned or rough feel to the hair due to, for example, the gradual removal of the natural or applied fats, lipids, or proteins contained in or at the surface of the hair.

Thus, a second composition, a hair conditioner which is generally a rinse-off product, can be used on hair after it has been shampooed in order to confer conditioning, smoothing, and softening properties to the hair. Aside from such properties, it is highly desirable to design conditioners that can confer other cosmetic benefits such as those provided by hair styling products, for example gels and mousses that are leave-in compositions that impart volume and body while on the hair. Some leave-in styling products use polymers, for example film-forming polymers, to provide volumizing properties. However, some polymers can be easily removed from the hair, for example by rinsing or washing. Thus, any cosmetic benefits to the hair from such products are generally diminished or removed once the hair is rinsed or washed.

Thus the present disclosure relates to hair conditioning compositions. More particularly, the embodiments of the disclosure relate to rinse-off compositions that provide volumizing properties on keratinous substrates, such as keratin fibers, in particular hair, wherein the volumizing effects on hair can be long-lasting, that is, the effect remains even after repeated washings or cleansing using the compositions of the present disclosure. The disclosure also relates to a hair conditioning process using this composition.

It is also an object of embodiments of the disclosure to provide a stable rinse-off composition that conditions a keratinous substrate while imparting increased mass, body or volume and maintaining desirable or cosmetically acceptable deposition and film formation capability on hair fibers to provide excellent volumizing and cosmetic properties, for example long-lasting volume, conditioning, softness and detangling.

Another object of the embodiments of the disclosure is to provide compositions that are translucent in appearance, an attribute that is desired by consumers. The visual appearance of translucency is typically associated with the sensation of a product being light weight on keratinous substrates such as hair (i.e., does not weigh the hair down), as well as with a clean feel on the hair, resulting in a perception of a volumizing or mass effect.

According to embodiments of the disclosure, a composition for treating and/or conditioning hair is provided, the composition comprising a cationic agent comprising at least two quaternary ammonium compounds; a modified starch, silane compounds, a cationic vinylpyrrolidone polymer, and water, wherein when the composition contains a long chain fatty alcohol, the fatty alcohol is present in an amount not more than 1% by weight of, based on the total weight of the composition. It has now been surprisingly and unexpectedly discovered that such a composition is stable, it is translucent in appearance, and delivers instant as well as long lasting mass, body, and/or volume to hair. Hair treated and/or contacted with the compositions according to embodiments of the disclosure was found to have improved mass, body, volume, to be easily rinsed, to dry fast and to stay clean longer while providing cosmeticity to the hair. At the same time, the hair is sufficiently conditioned.

Also disclosed is a process for imparting conditioning and other cosmetic properties to keratinous substrates such as the hair and/or the scalp using the composition according to embodiments of the disclosure, the process including applying to the keratinous substrates and/or scalp, a composition as defined above, rinsing off the composition, and optionally drying said keratinous substrates.

Other subjects, characteristics, aspects and advantages of embodiments of the disclosure will emerge even more clearly on reading the description and the various examples that follow.

BRIEF SUMMARY

Embodiments of the disclosure relate to a composition for treating keratinous substrates, the composition comprising:
(a) a cationic agent comprising:
(i) a first quaternary ammonium compound, including its salts, of the general formula (I):

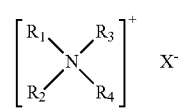

(I)

wherein $R_1$ and $R_4$, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among $R_1$, $R_2$, $R_3$ and $R_4$ denoting a radical comprising from 8 to 30 carbon atom; and X"" is chosen from halides, phosphates, acetates, lactates, (C2-C6) alkyl sulfates, and alkyl- or alkylaryl-sulfonates; and (ii) a second quaternary ammonium compound, including its salts, chosen from quaternary ammonium compounds of imidazoline of the general formula (II):

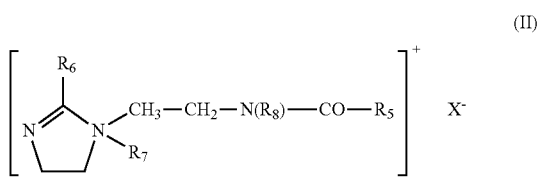

wherein $R_5$ and $R_6$ are chosen from alkenyl and alkyl radicals comprising from 8 to 30 carbon atoms or alkenyl and alkyl radicals derived from palm oil or hydrogenated tallow; $R_6$ is chosen from hydrogen, C1-C4 alkyl radicals, and alkenyl and alkyl radicals comprising from 8 to 30 carbon atoms; $R_7$ is chosen from C1-C4 alkyl radicals; $R_8$ is chosen from hydrogen and C1-C4 alkyl radicals; and X" is chosen from halides, phosphates, acetates, lactates, alkyl sulfates, alkyl sulfonates, and alkylaryl sulfonates;

(b) at least one modified starch;

(c) a first silane compound corresponding to formula (Ib):

$$R_1Si(OR_2)_z(R_3)_x(OH)_y \quad (Ib)$$

in which:

$R_1$ is a cyclic or acyclic, linear or branched, saturated or unsaturated $C_1$-$C_{22}$, in particular $C_2$-$C_{20}$, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for R1 to be interrupted with a heteroatom (O, S or NH) or a carbonyl group (CO), $R_2$ and $R_3$, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3;

(d) a second silane compound other than the first silane compound (c);

(e) at least one cationic vinylpyrrolidone polymer; and (f) water.

Embodiments of the disclosure also relate to a process for conditioning a keratinous substrate, such as hair and/or the scalp, involving applying the above-described composition onto the keratinous substrate, and to methods of increasing the volume of the keratinous substrate such as hair by treating or contacting with the hair above-described composition.

In certain embodiments, when the composition contains a fatty alcohol, the fatty alcohol is present in an amount not more than 1% by weight of, based on the total weight of the composition.

The compositions of embodiments of the disclosure are stable overtime and do not undergo phase separation. In addition, the compositions are translucent in appearance.

It is to be understood that both the foregoing general description and the following detailed description are exemplary and explanatory only, and are not restrictive of the disclosure.

BRIEF DESCRIPTION OF THE DRAWINGS

FIG. 1 is an image of a mannequin head showing the volumizing and root lift effects on the mannequin's hair.

It should be understood that the various aspects are not limited to the arrangements and instrumentality shown in the drawings.

DETAILED DESCRIPTION

As used herein, the expression "at least one" means one or more and thus includes individual components as well as mixtures/combinations.

In the present patent application, a species is termed as being "cationic" when it bears at least one permanent positive charge or when it can be ionized as a positively charged species, under the conditions of use of the compositions of embodiments of the disclosure (for example the medium or the pH) and not comprising any anionic filler.

A species is termed as being "nonionic" when it is neither cationic nor anionic within the meaning of the disclosure, in particular when it comprises no cationic or anionic groups within the meaning of the disclosure.

A species is termed as being "anionic" when it bears at least one permanent negative charge or when it can be ionized as a negatively charged species, under the conditions of use of the compositions of embodiments of the disclosure (for example the medium or the pH) and not comprising any cationic filler.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

The term "comprising" (and its grammatical variations) as used herein is used in the inclusive sense of "having" or "including" and not in the exclusive sense of "consisting only of".

"Keratinous substrates" as used herein, includes, but is not limited to keratin fibers such as hair on the human head and hair comprising eyelashes. "Keratinous substrates" as used herein, may also refer to the skin such as lips, finger nails or toe nails, and the scalp.

As used herein, the terms "applying a composition onto "keratinous substrates" as used herein, includes, and "applying a composition onto "keratinous substrates" or "keratin fibers" such as hair on a human head with at least one of the compositions of the disclosure, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions of the present disclosure onto keratinous substrates such as hair. The term "treat" (and its grammatical variations) as used herein also refers to contacting keratinous substrates such as hair with the compositions of the present disclosure onto "Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

The term "polymer" is understood to mean, within the meaning of the disclosure, a compound characterized by the multiple repetition of one or more species of atoms or groups of atoms, known as monomers, linked to each other in amounts sufficient to provide a set of properties that do not vary markedly with the addition or removal of one or a few of the monomers.

The term "film-forming polymer" is understood to mean a polymer which is capable of forming, by itself alone or in the presence of an additional film-forming agent, a macroscopically continuous or semi-continuous film on a support, in particular on keratinous substances, such as a cohesive film.

The term "rinse-off" is used herein to mean that a keratinous substrate such as hair is rinsed and/or washed with water either after or during the application of a composition onto the keratinous substrate, and before drying and/or styling said keratinous substrate. At least a portion of the composition is removed from the keratinous substrate during the rinsing and/or washing. A "rinse-off" product refers to a composition such as a hair care composition that is rinsed and/or washed with water either after or during the application of the composition onto the keratinous substrate, and before drying and/or styling said keratinous substrate.

A "leave-on" product refers to a cosmetic composition such as a hair care composition that is applied to a keratinous substrate such as hair and not further subjected to a rinsing and/or washing step before drying and/or styling the substrate.

The term "translucent" as used herein refers to a material (phase or container) which allows light to pass through without making it possible to distinguish alphanumeric characters using 5 mm thick samples.

The term "translucent" as used herein also means that a material (phase or container) is sufficiently clear such that a pattern of one or more opaque phases may be observable.

The compositions and methods of the present disclosure can comprise, consist of, or consist essentially of the essential elements and limitations of the disclosure described herein, as well as any additional or optional ingredients, components, or limitations described herein or otherwise useful.

An embodiment of the present disclosure is directed to a composition for treating keratinous substrates, the composition comprising:

(a) a cationic agent comprising:
  (i) a first quaternary ammonium compound, including its salts, of the general formula (I):

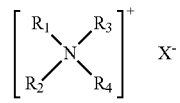

(I)

wherein $R_1$ and $R_4$, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among $R_1$, $R_2$, $R_3$ and $R_4$ denoting a radical comprising from 8 to 30 carbon atom; and X"" is chosen from halides, phosphates, acetates, lactates, (C2-C6) alkyl sulfates, and alkyl- or alkylaryl-sulfonates; and (ii) a second quaternary ammonium compound, including its salts, chosen from quaternary ammonium compounds of imidazoline of the general formula (II):

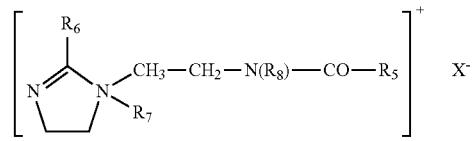

(II)

wherein $R_5$ and $R_6$ are chosen from alkenyl and alkyl radicals comprising from 8 to 30 carbon atoms or alkenyl and alkyl radicals derived from palm oil or hydrogenated tallow; $R_6$ is chosen from hydrogen, C1-C4 alkyl radicals, and alkenyl and alkyl radicals comprising from 8 to 30 carbon atoms; $R_7$ is chosen from C1-C4 alkyl radicals; $R_8$ is chosen from hydrogen and C1-C4 alkyl radicals; and X" is chosen from halides, phosphates, acetates, lactates, alkyl sulfates, alkyl sulfonates, and alkylaryl sulfonates;

(b) at least one modified starch;
(c) a first silane compound corresponding to formula (Ib):

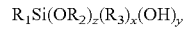

$R_1Si(OR_2)_z(R_3)_x(OH)_y$ (Ib)

in which:
$R_1$ is a cyclic or acyclic, linear or branched, saturated or unsaturated $C_1$-$C_{22}$, in particular $C_2$-$C_{20}$, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for R1 to be interrupted with a heteroatom (O, S or NH) or a carbonyl group (CO), $R_2$ and $R_3$, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3;

(d) a second silane compound other than the first silane compound (c);

(e) at least one cationic vinylpyrrolidone polymer and (f) water.

In another embodiment of the present disclosure, the composition is a rinse-off composition for conditioning keratinous substrates, in particular hair, wherein the composition comprises:

(a) from about 2% to about 7% by weight of a cationic agent comprising:

(i) a first quaternary ammonium compound, including its salts of the general formula (I):

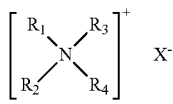

(I)

wherein $R_1$ and $R_4$, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among $R_1$, $R_2$, $R_3$ and $R_4$ denoting a radical comprising from 8 to 30 carbon atom; and X"" is chosen from halides, phosphates, acetates, lactates, (C2-C6) alkyl sulfates, and alkyl- or alkylaryl-sulfonates; and (ii) a second quaternary ammonium compound, including its salts, selected from quaternary ammonium compounds of imidazoline of the general formula (II):

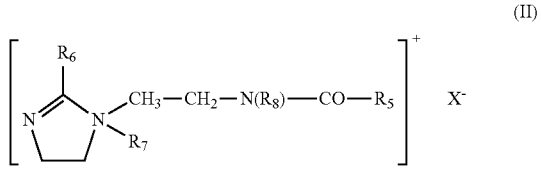

(II)

wherein $R_5$ and $R_6$ are chosen from alkenyl and alkyl radicals comprising from 8 to 30 carbon atoms or alkenyl and alkyl radicals derived from palm oil or hydrogenated tallow; $R_6$ is chosen from hydrogen, C1-C4 alkyl radicals, and alkenyl and alkyl radicals comprising from 8 to 30 carbon atoms; $R_7$ is chosen from C1-C4 alkyl radicals; $R_8$ is chosen from hydrogen and C1-C4 alkyl radicals; and X" is chosen from halides, phosphates, acetates, lactates, alkyl sulfates, alkyl sulfonates, and alkylaryl sulfonates;

(b) from about 3.5% to about 7.5% by weight of at least one modified starch;

(c) from about 0.2% to about 3% by weight of a first silane compound corresponding to formula (Ib):

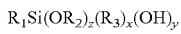

(Ib)

in which:

$R_1$ is a cyclic or acyclic, linear or branched, saturated or unsaturated $C_1$-$C_{22}$, in particular $C_2$-$C_{20}$, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for $R_1$ to be interrupted with a heteroatom (O, S or NH) or a carbonyl group (CO), $R_2$ and $R_3$, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3;

(d) from about 0.1% to about 1% by weight of a second silane compound chosen from amino silicones other than the first silane (c);

(e) at least one cationic vinylpyrrolidone polymer chosen from polyquaternium 11; and (f) water;

all weights being based on the total weight of the composition; and wherein when the composition contains a fatty alcohol, the fatty alcohol is present in an amount not more than 1% by weight of, based on the total weight of the composition; and all weights being based on the total weight of the composition.

In an embodiment, the first quaternary ammonium compound comprising the cationic agent salts is chosen from quaternary ammonium compounds of the general formula (I) as described above.

In particular embodiments, the first quaternary ammonium compound is chosen from behentrimonium chloride, cetrimonium chloride, behentrimonium methosulfate, and mixtures thereof.

In particular embodiments, the cationic agent comprises a first quaternary ammonium compound, including its salts, of the general formula (I) as described above and a second quaternary ammonium compound, including its salts, of imidazoline of the general formula (II) as described above.

In some embodiments, the cationic agent comprises a first quaternary ammonium compound chosen from behentrimonium chloride, cetrimonium chloride, behentrimonium methosulfate, and mixtures thereof and a second quaternary ammonium compound chosen from quaternium-83, quaternium-87, and mixtures thereof.

In preferred embodiments, the cationic agent comprises a first quaternary ammonium compound chosen from behentrimonium chloride and a second quaternary ammonium compound chosen from quaternium-87.

In an embodiment, the modified starch is chosen hydroxypropyl starch phosphate, starch acetate, sodium tripolyphosphate, sodium orthophosphate, phosphorus oxychloride or sodium trimetaphosphate, and mixtures thereof, and mixtures thereof, and is preferably chosen from hydroxypropyl starch phosphate.

In one embodiment, first silane compound is an alkoxysilane, preferably chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane or their oligomers thereof, and mixtures thereof. In particular embodiments, the first silane compound is 3-aminopropyltriethoxysilane (APTES).

In another embodiment, the second silane compound is chosen from amino silicones other than the first silane and comprising at least one primary, secondary or tertiary amine or a quaternary ammonium group, preferably from amodimethicones, or preferably from amino silicones (micro emulsions) having at least one quaternary ammonium group, such as for example, silicone quaternium-16, and mixtures thereof.

In certain embodiments, the amino silicone comprising the second silane of the present disclosure is provided as a microemulsion containing at least one surfactant chosen from nonionic surfactants, cationic surfactants, and mixtures thereof.

The compositions according to various embodiments of the disclosure have a homogenous texture, i.e., not lumpy, and are easy to apply and spread on the hair.

It has been surprisingly and unexpectedly discovered that the compositions according to the disclosure are stable over time, exhibit no visible phase separation, are translucent in appearance, and allow retention of the cosmetic effects of the cationic agents and the first and second silane compounds, such that hair is effectively or satisfactorily volumized and easy to detangle and comb through after treatment with the composition. It is possible that the volumizing effect imparted to the hair remains even after several washings of the hair.

Cationic Agent

The cationic agent of the present disclosure comprises at least two quaternary ammonium compounds, including their salts, wherein the first quaternary ammonium compounds is chosen from:

(A) quaternary ammonium compounds, including their salts, of the general formula (I) below:

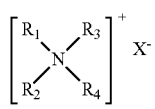

(I)

wherein $R_1$ and $R_4$, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among $R_1$, $R_2$, $R_3$ and $R_4$ denoting a radical comprising from 8 to 30 carbon atom; and X"" is chosen from halides, phosphates, acetates, lactates, (C2-C6) alkyl sulfates, and alkyl- or alkylaryl-sulfonates; and the second quaternary ammonium compound is chosen from quaternary ammonium compounds, including their salts, salts of imidazoline (also called imidazolium compound) of the general formula (II);

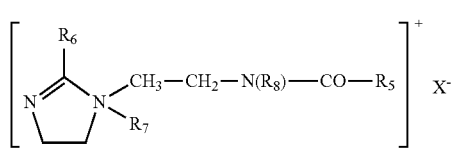

(II)

wherein $R_5$ and $R_6$ are chosen from alkenyl and alkyl radicals comprising from 8 to 30 carbon atoms or alkenyl and alkyl radicals derived from palm oil or hydrogenated tallow $R_6$ is chosen from hydrogen, C1-C4 alkyl radicals, and alkenyl and alkyl radicals comprising from 8 to 30 carbon atoms; $R_7$ is chosen from C1-C4 alkyl radicals; $R_8$ is chosen from hydrogen and C1-C4 alkyl radicals; and X" is chosen from halides, phosphates, acetates, lactates, alkyl sulfates, alkyl sulfonates, and alkylaryl sulfonates.

The first quaternary ammonium compound may be selected from behenyltrimethylammonium chloride (also called behentrimonium chloride), cetyltrimethylammonium chloride (also called cetrimonium chloride), quaternium-22, behenylamidopropyl-2, 3-di-hydroxypropyldimethylammonium chloride, palmitylamidopropyltrimethylammonium chloride, stearamidopropyldimethylamine, and chloride and methyl sulfate of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethyl-ammonium, and mixtures thereof.

Other examples of the first quaternary ammonium compounds include distearyldimethylammonium chloride, oleocetyldimethylhydroxyethylammonium chloride, stearamidopropyldimethyl (myristyl acetate) ammonium chloride, di(C1-C2 alkyl) (C12-C22 alkyl)hydroxy(C1-C2alkyl)ammonium salt, such as dialkyldimethylammonium or alkyltrimethylammonium salt in which the alkyl radical preferably comprises 12 to 24 carbon atoms, propanetallowdiammonium dichloride, behentrimonium methosulfate, and mixtures thereof.

Non-limiting examples of the first quaternary ammonium salts that comprise the cationic agent of the current compositions include in particular behentrimonium chloride, cetrimonium chloride, behentrimonium methosulfate, and mixtures thereof.

Non-limiting examples of the second quaternary ammonium salts that comprise the cationic agent of the current compositions include in particular quaternium-83, quaternium-87, and mixtures thereof.

A preferred second quaternary ammonium compound is Quaternium-87 (INCI name) sold under the tradename VARISOFT W 575 PG N by Evonik Goldschmidt. In an embodiment, the cationic agent comprises at least two quaternary ammonium compounds chosen from those of formula (I) and those of formula (II).

In a preferred embodiment, the cationic agent comprises at least two quaternary ammonium compounds chosen from behentrimonium chloride and quaternium-87.

In certain embodiments, the total amount of the cationic agent ranges from about 1% to about 10% by weight, such as from about 1.5% to about 8% by weight, from about 2% to about 7% by weight, from about 2% to about 6% by weight, or from about 3% to about 5.5%, by weight of active material, based on the total weight of the composition of the present disclosure, including all ranges and subranges therebetween.

In various embodiments, the total amount of the cationic agent is about 1%, 1.5%, 1.75%, 2%, 2.25%, 2.5%, 2.75%, 3%, 3.25%, 3.5%, 3.75%, 04%, 4.25%, 4.5%, 4.75%, 5%, 5.5%, 6%, 6.5%, 7%, 7.5%, 8%, 9%, and 10%, by weight of active material, based on the total weight of the composition of the present disclosure.

In certain embodiments, the amount of the first quaternary ammonium compound ranges from about 0.5% to about 5% by weight, such as from about 0.5% to about 4% by weight, from about 1% to about 3% by weight, from about 1% to about 2.5% by weight, or from about 1% to about 2%, by weight of active material, based on the total weight of the composition of the present disclosure, including all ranges and subranges therebetween.

In various embodiments, the amount of the first quaternary ammonium compound is about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, and 3% by weight of active material, based on the total weight of the composition of the present disclosure.

In certain embodiments, the amount of the second quaternary ammonium compound ranges from about 1% to about 5% by weight, such as from about 1.5% to about 5% by weight, from about 2% to about 5% by weight, from about 2.5% to about 5% by weight, or from about 3% to about 4%, by weight of active material, based on the total weight of the composition of the present disclosure, including all ranges and subranges therebetween.

In various embodiments, the amount of the second quaternary ammonium compound is about 1%, 1.5%, 1.75%, 2%, 2.25%, 2.5%, 2.75%, 3%, 3.25%, 3.5%, 3.75%, 4%, 4.25%, 4.5%, 4.75%, and 5%, by weight of active material, based on the total weight of the composition of the present disclosure.

Modified Starch

The composition of the invention comprises at least one modified starch. A modified starch is a starch that is been modified via processes known to those skilled in the art, for instance esterification, etherification, oxidation, acidic hydrolysis, crosslinking or enzymatic conversion. Non-limiting examples of modified starches include aluminium starch octenylsuccinate, sodium starch octenylsuccinate, calcium starch octenylsuccinate, distarch phosphate, hydroxyethyl starch phosphate, hydroxypropyl starch phosphate, sodium carboxymethyl starch and sodium starch glycolate.

Particularly preferred modified starches for use in the present invention are starch phosphates such as: monostarch phosphates of formula (Ia), Am—O—PO—(OX)$_2$ (Ia); distarch phosphates of formula (IIa), Am—O—PO—(OX)—O—Am (IIa); tristarch phosphates of the formula (IIIa), Am—O—PO—(O—Am)$_2$ (IIIa); and mixtures thereof, wherein:

Am represents starch; and

X represents alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

Particularly suitable starch phosphates which may be employed in the compositions of the present disclosure include, but are not limited to, hydroxypropyl starch phosphate, starch acetate, sodium tripolyphosphate, sodium orthophosphate, phosphorus oxychloride or sodium trimetaphosphate, and mixtures thereof.

A particularly preferred modified starch for use in the present invention is hydroxypropyl starch phosphate, commercially available under the tradename STRUCTURE ZEA, from Akzo Nobel.

The compositions of the disclosure preferably contain the modified starch in an amount of from about 3.5% to about 8% by weight, such as from about 3.5% to about 7.5% by weight, from about 3.5% to about 7% by weight, from about 4% to about 6.5% by weight, or from about 5% to about 6%, by weight of active material, based on the total weight of the composition, including all ranges and subranges therebetween.

In various embodiments, the total amount of the modified starch is about 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, and 8%, by weight of active material, based on the total weight of the composition.

First Silane Compound

According to the invention, the composition comprises a first silane compound corresponding to formula (Ib) and/or their oligomers thereof.

Formula (Ib) is as follows:

$$R_1Si(OR_2)_z(R_3)_x(OH)_y, \quad (Ib)$$

in which:

$R_1$ is a cyclic or acyclic, linear or branched, saturated or unsaturated $C_1$-$C_{22}$, in particular $C_2$-$C_{20}$, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for $R_1$ to be interrupted with a heteroatom (0, S or NH) or a carbonyl group (CO), $R_2$ and $R_3$, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3.

The term "oligomer" means the polymerization products of the compounds of formula (I) comprising from 2 to 10 silicon atoms.

Preferably, $R_1$ is a linear or branched, preferably linear, saturated $C_1$-$C_{22}$, in particular $C_2$-$C_{12}$, hydrocarbon-based chain, which may be substituted with an amine group $NH_2$ or NHR(R=$C_1$-$C_{20}$, in particular $C_1$-$C_6$, alkyl).

Preferably, $R_2$ represents an alkyl group comprising from 1 to 4 carbon atoms, better still a linear alkyl group comprising from 1 to 4 carbon atoms, and preferably the ethyl group.

Preferably, z ranges from 1 to 3.

Preferably, y=0.

Preferentially, z=3, and therefore x=y=0.

In one embodiment of the invention, $R_1$ represents a linear alkyl group comprising from 7 to 18 carbon atoms and more particularly from 7 to 12 carbon atoms, or a $C_1$-$C_6$, preferably $C_2$-$C_4$, aminoalkyl group. More particularly, $R_1$ represents an octyl group.

In one embodiment of the invention, $R_1$ is a linear or branched, saturated or unsaturated $C_1$-$C_{22}$ hydrocarbon-based chain, substituted with an amine group $NH_2$ or NHR (R=$C_1$-$C_{20}$, in particular $C_1$-$C_6$, alkyl, $C_3$-$C_{40}$ cycloalkyl or $C_6$-$C_{30}$ aromatic). In this variant, $R_1$ preferably represents a $C_1$-$C_6$, preferably $C_2$-$C_4$, aminoalkyl group.

Preferably, the first silane compound of the present invention is an alkoxysilane.

Preferably, the composition comprises at least one compound of formula (Ib) chosen from alkoxysilanes such as 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane, N-(2-aminoethylaminomethyl)phenethyltrimethoxysilane, and mixtures thereof.

In certain embodiments, the silane of the disclosure is an alkoxysilane selected from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane or oligomers thereof, and mixtures thereof.

In preferred embodiments, the first silane compound of the present invention is chosen from 3-aminopropyltriethoxysilane (APTES) or oligomers thereof, or mixtures thereof.

The first silane compound used in the composition of the invention, in particular those comprising a basic function, may be partially or totally neutralised in order to improve the water-solubility thereof. In particular, the neutralising agent may be chosen from organic or inorganic acids, such as citric acid, tartaric acid, lactic acid or hydrochloric acid.

Preferably, the optionally neutralised silanes according to the invention are water-soluble and in particular soluble at a concentration of 2%, better still at a concentration of 5% and even better still at a concentration of 10% by weight in water at a temperature of 25° C. and at atmospheric pressure (1 atm). The term "soluble" is intended to mean the formation of a single macroscopic phase.

The silane(s) of formula (Ib) and/or oligomers thereof may be present in the composition according to the invention in an amount of about 0.05% to about 5% by weight, such as from about 0.1% to about 4% by weight, from about 0.2% to about 3% by weight, from about 0.3% to about 2% by weight, from about 0.4% to about 1%, or from about 0.4% to less than 1%, such as from about 0.4% to about 0.8%, by weight of active material, based on the total weight of the composition, including all ranges and subranges therebetween.

In various embodiments, the total amount of the silane(s) of formula (Ib) is about 0.05%, 0.075%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, 2%, 2.25%, 2.5%, 2.75%, 3%, 3.5%, 4%, 4.5%. 5% by weight of active material, based on the total weight of the composition.

Second Silane Compound

The second silane compound of the present disclosure is chosen from silicones which are compounds other than the first silane compounds described above. These silicones may be chosen from amino silicones and dimethicone.

In certain embodiments, the second silane compound of the present disclosure is an amino silicone.

The term "amino silicone" is intended to mean any silicone comprising at least one primary, secondary or tertiary amine or a quaternary ammonium group (i.e., a quaternized group).

As amino silicone that may be used in the scope of the instant disclosure, the following can be cited:

a) polysiloxanes corresponding to formula (A):

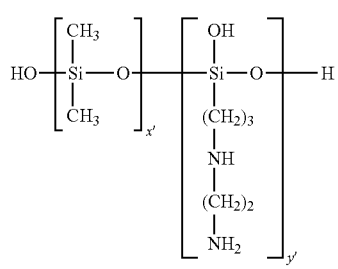

(A)

in which x' and y' are integers such that the weight-average molecular weight (Mw) is comprised between about 5000 and 500 000;

b) amino silicones corresponding to formula (B):

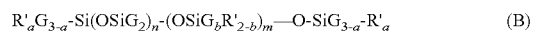

$R'_a G_{3-a}\text{-Si}(OSiG_2)_n\text{-}(OSiG_b R'_{2-b})_m\text{—O-SiG}_{3-a}\text{-}R'_a$ (B)

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula —$C_qH_{2q}L$ in which q is a number ranging from 2 to 8 and L is an optionally quaternized amino group chosen from the following groups:

—NR"-Q-N(R")$_2$

—N(R")$_2$

—N+(R")$_3$A-

—N+H(R")$_2$A-

—N+H$_2$(R") A-

—N(R")-Q-N+R"H$_2$A-

—NR"-Q-N+(R")$_2$H A-

—NR"-Q-N+(R")$_3$A-, in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A- represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

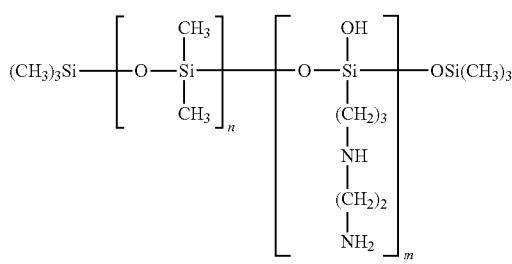

(C)

in which n and m have the meanings given above, in formula B.

Another group of amino silicones corresponding to this definition is represented by silicones having the following formulae (D) or (E):

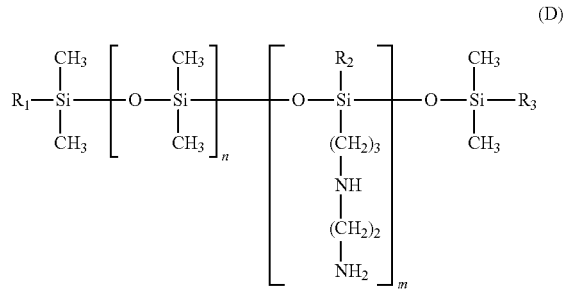

(D)

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

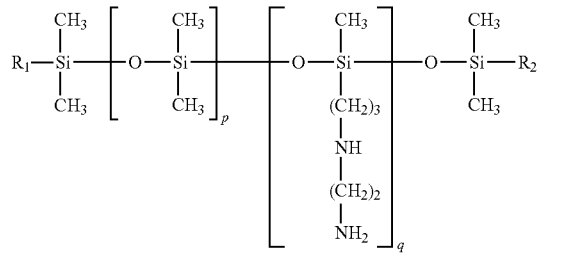

(E)

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

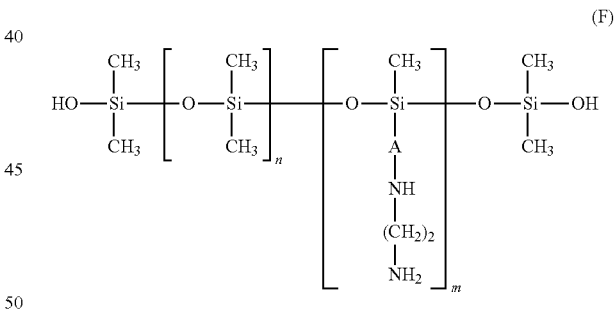

(F)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

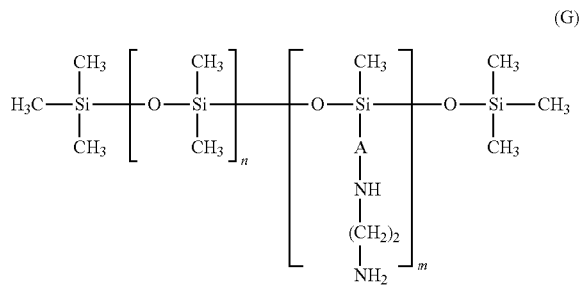
(G)

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

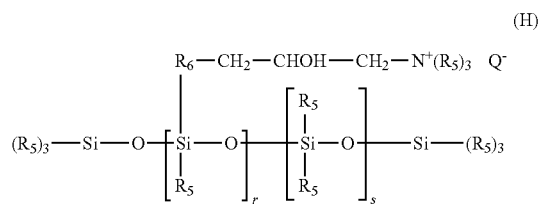
(H)

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in U.S. Pat. No. 4,185,087.

d) quaternary ammonium silicones having formula (I):

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_1$ alkyl radical, a $C_2$-$C_{18}$ alkenyl radical or a —$R_6$—NHCOR$_7$ radical;

X— is an anion such as a halide ion, in particular chloride, or an organic acid salt (for example acetate);

r represents a mean statistical value from 2 to 200 and in particular from 5 to 100;

These silicones are described, for example, in patent application EP-A 0 530 974.

e) amino silicones having formula (J):

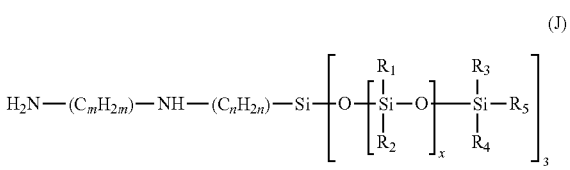
(J)

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

f) multiblock polyoxyalkylenated amino silicones, of type (AB)n, A being a polysiloxane block and B being a polyoxyalkylenated block containing at least one amine group.

Said silicones are preferably constituted of repeating units having the following general formulae:

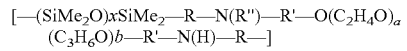

or alternatively

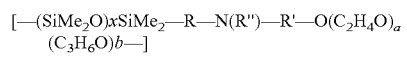

in which:

a is an integer greater than or equal to 1, preferably ranging from 5 to 200, more particularly ranging from 10 to 100;

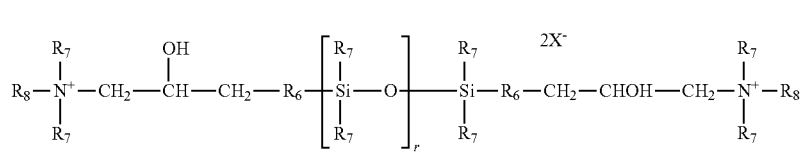
(I)

b is an integer comprised between 0 and 200, preferably ranging from 4 to 100, more particularly between from 5 and 30;

x is an integer ranging from 1 to 10 000, more particularly from 10 to 5000;

R" is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names Silsoft™ A-843 or Silsoft™ A+ by Momentive.

g) the alkylamino silicones corresponding to formula (K) below:

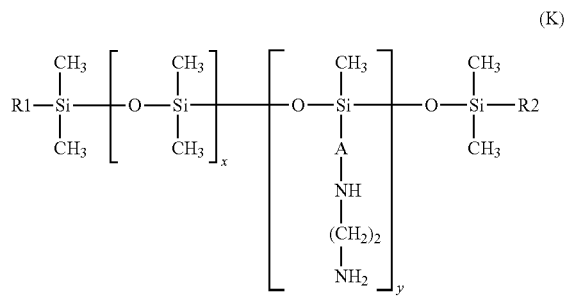

(K)

in which:

x and y are numbers ranging from 1 to 5000; preferably, x ranges from 10 to 2000 and especially from 100 to 1000; preferably, y ranges from 1 to 100;

$R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;

A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —$CH_2CH_2CH_2$ and —$CH_2CH(CH_3)CH_2$—.

Preferably, $R_1$ and $R_2$, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, $R_1$ and $R_2$, which may be identical or different, are chosen from hexadecyl (cetyl) and octadecyl (stearyl) radicals.

Preferentially, the silicone is of formula (K) with:

x ranging from 10 to 2000 and especially from 100 to 1000;

y ranging from 1 to 100;

A comprising 3 to 6 carbon atoms and especially 4 carbon atoms; preferably, A is branched; and more particularly A is chosen from the following divalent radicals: $CH_2CH_2CH_2$ and —$CH_2CH(CH_3)CH_2$—; and $R_1$ and $R_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

h) silicone compounds with at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Most preferred are quaternium 80, silicone quaternium-16, silicone quaternium-18, silicone quaternium-15, and mixtures thereof.

The silicone compounds with at least one quaternary ammonium group can also include those compounds of formula (B) when L in formula (B) is a quaternized amino group as described.

The second silane compound of the present disclosure may be provided or may be commercially available in emulsion form, that further comprises surfactants chosen from nonionic surfactants, cationic surfactants, and mixtures thereof. In certain embodiments, the emulsion in which the second silane is contained is a microemulsion.

Preferably, the second silane compound chosen from amino silicones according to the invention are selected from the amino silicones comprising at least one primary, secondary or tertiary amine and from silicone compounds having at least one quaternary ammonium group, and mixtures thereof. Preferred amino silicones comprising at least one primary, secondary or tertiary amine are chosen from amodimethicone (INCI name) sold under the tradename SILSOFT 253, by Momentive Performance Materials or under the tradename XIAMETER® MEM-8299 Cationic Emulsion by Dow Corning or under the tradename Dow Corning 2-8566 Amino Fluid by Dow Corning, bis-isobutyl/PEG/PPG-20/35/amodimethicone copolymer, bis-cetearyl amodimethicone, bis-amino PEG/PPG-41/3 aminoethyl PG-propyl dimethicone (e.g., Silsoft A-843), PEG-40/PPG-8 methylaminopropyl hydroxypropyl dimethicone copolymer (e.g., Silsoft A+), bis-isobutyl/PEG/PPG-20/35/amodimethicone copolymer (e.g., Dow Corning CE 8401 Emulsion), or mixtures thereof. A preferred silicone compound with at least one quaternary ammonium group is silicone quaternium-16 (INCI name) sold under the tradename DOW CORNING CE-7114 SILICONE QUAT MICROEMULSION (previously known as XX-7113), supplied by Dow Corning.

The second silane compound(s) may be present in the composition according to the invention in an amount of about 0.05% to about 2% by weight, such as from about 0.1% to about 1.5% by weight, from about 0.1% to about 1% by weight, from about 0.2% to about 0.9% by weight, or from about 0.4% to about 0.9%, by weight of active material, based on the total weight of the composition, including all ranges and subranges therebetween.

In various embodiments, the total amount of the second silane compound is about 0.05%, 0.075%, 0.1%, 0.15%, 0.2%, 0.25%, 0.3%, 0.33%, 0.35%, 0.4%, 0.44%, 0.45%, 0.5%, 0.55%, 0.6%, 0.65%, 0.7%, 0.75%, 0.8%, 0.85%, 0.88%, 0.9%, 0.95%, 1%, 1.25%, 1.5%, 1.75%, and 2% by weight of active material, based on the total weight of the composition.

Cationic Vinylpyrrolidone Polymer

The at least one cationic vinylpyrrolidone polymer of the present disclosure may be chosen from vinylpyrrolidone/dimethylaminoethyl methacrylate copolymers quaternized with diethyl sulfate, polymeric quaternary ammonium salt consisting of vinylpyrrolidone and dimethylaminopropyl methacrylamide monomers, and mixtures thereof.

In some embodiments, the cationic vinylpyrrolidone polymer of the present disclosure is chosen from vinylpyrrolidone/dimethylaminoethyl methacrylate copolymers quaternized with diethyl sulfate such as polyquaternium-11 (INCI name), commercially available from A & E Connock (Perfumery & Cosmetics) or under the tradenames DEHYQUART CC 11 OR LUVIQUAT PQ 11 PN (BASF Corporation) or GAFQUAT 440 OR GAFQUAT 734 OR GAFQUAT 755 OR GAFQUAT 755N (Ashland Inc.) or ORISTAR PQ11 (Orient Stars LLC) or POLYQUAT-11 SL (Sino Lion (USA) Ltd.) or TRiquat 11N-CC (TRI-K Industries, Inc., A Member of the Galaxy Group)

In other embodiments, the cationic vinylpyrrolidone polymer of the present disclosure is chosen from a polymeric quaternary ammonium salt consisting of vinylpyrrolidone and dimethylaminopropyl methacrylamide monomers such as polyquaternium-28 (INCI name) commercially available from A & E Connock (Perfumery & Cosmetics) or under the tradenames CONDITIONEZE NT-20 (Ashland Inc.) OR GAFQUAT HS-100 (Ashland Inc.).

The cationic vinylpyrrolidone polymer may be present in the composition according to the invention in an amount of about 0.05% to 5% by weight, such as from about 0.075% to about 4% by weight, from about 0.1% to about 3% by weight, from about 0.1% to about 2% by weight, from about 0.1% to about 1%, or from about 0.05% to less than 1% by weight, such as from about 0.05% to about 0.8% by weight of active material, based on the total weight of the composition, including all ranges and subranges therebetween.

In various embodiments, the total amount of the cationic vinylpyrrolidone polymer is about 0.05%, 0.075%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, 2%, 2.25%, 2.5%, 2.75%, 3%, 3.5%, 4%, 4.5%, 5% by weight of active material, based on the total weight of the composition.

Water

The compositions according to various embodiments of the disclosure may be aqueous. Water can be present in amounts of about 95% or less, such as from about 95% to about 5% by weight, or about 90%, 80%, 70%, 60%, 50%, 40%, 30%, 20%, 10%, or 5% or less, by weight, based on the total weight of the composition. In further embodiments, water can be present in an amount of about 95%, such as about 90%, 80%, 70%, 60%, 50%, 40%, 30%, 20%, 10%, or 5%, by weight, based on the total weight of the composition, including all ranges and subranges therebetween. Additionally, water can be present in the compositions of the present disclosure in the amount of from about 20% to about 95% by weight, from about 40% to about 90% by weight, or from about 50% to about 80% by weight, based on the total weight of the compositions.

In other embodiments, water can be present in the compositions of the present disclosure in the amount of at least about 95%, 90%, 80%, 70%, 60%, 50%, 45%, 40%, 30%, 20%, 10%, 5% by weight, based on the total weight of the compositions.

Fatty Alcohol

The compositions of the present disclosure may further comprise at least one fatty alcohol. The fatty alcohols that may be used in the composition of the disclosure include, but are not limited to, non-alkoxylated, saturated or unsaturated, linear or branched, and have from 6 to 30 carbon atoms and more particularly from 8 to 30 carbon atoms; for example, cetyl alcohol, stearyl alcohol and their mixture (cetearyl alcohol), octyldodecanol, 2-butyloctanol, 2-hexyldecanol, 2-undecylpentadecanol, oleic alcohol or linoleic alcohol.

In some embodiments, the compositions of the present invention contain at least one fatty alcohol.

In other embodiments, the compositions of the present invention contain at least one fatty alcohol present in an amount not more than 1% by weight, such as in an amount from between about 0.1 to about 1% by weight, or such as in an amount from between about 0.2 to about 0.75% by weight, or such as in an amount from between about 0.2 to about 0.5% by weight of active material, based on the total weight of the composition.

In yet other embodiments, the compositions of the present invention are substantially free of fatty alcohol compounds. The term "substantially free of fatty alcohol compounds" as used herein means that the amount by weight of the fatty alcohol in the compositions of the present invention is less than about 0.5%, or less than about 0.4%, or less than about 0.3% by weight of active material, based on the total weight of the composition.

pH

The pH of the compositions according to the disclosure generally ranges from about 3 to about 7, for example from about 5 to about 6.5, or from about 5 to about 6.0, or from about 3.5 to about 4.5, including ranges and subranges therebetween. In certain embodiments, the pH of the compositions according to the disclosure is at about 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.2, 6.4, 6.6, 6.8, and 7.

Additional Components

The composition according to the disclosure may also comprise additives chosen from cationic polymers other than the claimed cationic compounds, nonionic polymers, rheology modifiers, thickening and/or viscosity modifying agents, associative or non-associative polymeric thickeners, non-polymeric thickeners, non-polymeric surfactants (non-ionic, cationic or amphoteric), nacreous agents, dyes or pigments, fragrances, mineral, plant or synthetic oils, waxes, vitamins, proteins including ceramides, vitamins, UV-screening agents, free-radical scavengers, antidandruff agents, hair-loss counteractants, hair restorers, preserving agents, pH stabilizers and solvents, and mixtures thereof. A person skilled in the art will take care to select the optional additives and the amount thereof such that they do not harm the properties of the compositions of the present disclosure.

If present in the composition, these additives are generally present in an amount ranging up to about 40% by weight of active material relative to the total weight of the composition, such as up to about 30%, up to about 20%, up to about 15%, up to about 10%, up to about 5%, such as from 0% to 20%.

The compositions of certain embodiments may comprise stabilizers, for example sodium chloride, magnesium dichloride or magnesium sulfate.

The rheology modifiers and thickening/viscosity-modifying agents that may be employed in compositions of the present disclosure may include any water-soluble or water-dispersible compound that is compatible with the compositions of the disclosure, such as acrylic polymers, non-acrylic polymers, starch, cellulose-based polymers, non-polymeric and polymeric gelling agents, and mixtures thereof.

The compositions may be packaged in various forms, especially in bottles, in pump bottles or in tubes or in jars or in aerosol containers so as to apply the composition in vaporized form or in the form of a mousse. The compositions may also impregnate applicators, especially gloves or wipes.

The composition may be applied by hand, with an applicator nozzle, with a container equipped with a pump and a dispensing comb, or with an insoluble substrate impregnated with the composition.

Processes/Methods

The compositions according to the disclosure may be prepared according to techniques that are well known to those skilled in the art.

Embodiments of the disclosure also relate to a process for treating keratinous materials, such as hair, which consists in applying an effective amount of a composition as defined above to the said keratinous materials, and in rinsing, for example with water, after an optional leave-on time.

Certain embodiments also relate to a process for conditioning keratinous materials, which consists in applying an effective amount of a composition as defined above to the said keratinous materials, and in optionally rinsing, for example with water, after an optional leave-on time.

In some embodiments, keratinous materials, such as hair, may be washed or cleansed by a first step of applying a shampoo or cleansing or detergent-based composition, with an optional leave-on time, followed by a second step of applying the composition of the disclosure onto hair, with an optional step of rinsing the hair with water between the two first and second steps, and optionally rinsing the composition of the disclosure, for example with water, after an optional leave-on time.

The compositions may be applied to keratinous substrates, such as the hair, and subsequently rinsed off. In various embodiments, the compositions comprise hair care compositions for conditioning the hair, and in various embodiments the hair care composition will traditionally be rinsed off the hair within a short period of time after application to the hair, such as a period of time up to about 10 minutes, up to about 5 minutes, or up to about 2 minutes after application to the hair.

In various embodiments, processes according to the disclosure comprise applying the compositions described onto keratinous substrates, such as the hair, and subsequently rinsing the compositions off. The processes may, in various embodiments, impart conditioning and/or volume to the keratinous substrate to which the composition is applied, even after the composition is rinsed off. The processes may additionally impart long lasting volume as well as conditioning to the keratinous substrates.

As used herein, the method/process and composition disclosed herein may be used on the hair that has not been artificially dyed, pigmented or permed.

As used herein, the method/process and composition disclosed herein may be also used on the hair that has been artificially dyed, pigmented or permed.

EXAMPLES

The following Examples are intended to be non-restrictive and explanatory only, with the scope of the disclosure being defined by the claims.

The ingredient amounts in the compositions/formulas described below are expressed in % by weight, based on the total weight of the composition/formula.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective measurements. The following examples are intended to illustrate the disclosure without limiting the scope as a result.

Example 1: Compositions

TABLE 1

| | Conditioner Compositions | | | | | |
|---|---|---|---|---|---|---|
| INCI US | Formula A % by weight | Formula B % by weight | Formula C % by weight | Formula D % by weight | Formula E % by weight | Formula F % by weight |
| BEHENTRIMONIUM CHLORIDE[a] (79% by weight active) | 1.875 | 1.875 | 1.875 | 1.875 | 1.875 | 1.875 |
| QUATERNIUM-87[b] (75% by weight active) | 4.02 | 4.02 | 4.02 | 4.02 | 4.02 | 4.02 |
| HYDROXYPROPYL STARCH PHOSPHATE[c] (88% by weight active) | 7 | 7 | 7 | 7 | 6 | 6 |
| AMINOPROPYL TRIETHOXYSILANE[d] | 0.5 | 0.5 | 0.5 | 0.5 | 0.5 | 0.5 |
| SILICONE MICROEMULSION 1 (AMODIMETHICONE and C11-15 PARETH-7 and LAURETH-9 and GLYCERIN and) TRIDECETH-12[e] 17.2% by weight active) | | 2 | | 2 | | 2 |
| SILICONE MICROEMULSION 2 (SILICONE QUATERNIUM-16 and UNDECETH-11 and BUTYLOCTANOL and UNDECETH-5 and ACETIC ACID[f] 22% by weight active) | 2 | | 2 | | 2 | |
| POLYQUATERNIUM-11[g] (20% by weight active) | 0.5 | 0.5 | 0.5 | 0.5 | 0.5 | 0.5 |
| POLYQUATERNIUM-37 (and) PROPYLENE GLYCOL DICAPRYLATE/ DICAPRATE (and) PPG-1 TRIDECETH-6[h] (50% by weight active) | 0.1 | 0.1 | 0.1 | 0.1 | 0.1 | 0.1 |
| ORGANIC SOLVENT | 5 | 5 | 5 | 5 | 5 | 5 |
| COLORANTS | | | 0.000037 | 0.000037 | 0.00008 | 0.00008 |
| FATTY ALCOHOL | 0.25 | 0.25 | 0.25 | 0.25 | 0.25 | 0.25 |
| FRAGRANCE | 0.8 | 0.8 | 0.8 | 0.8 | 0.8 | 0.8 |
| PRESERVATIVES | 0.7 | 0.7 | 0.7 | 0.7 | 0.7 | 0.7 |
| WATER | Q.S. 100 | Q.S. 100 | Q.S. 100 | Q.S. 100 | Q.S. 100 | Q.S. 100 |

[a]available from many suppliers
[b]known by the tradename VARISOFT W 575 PG N, supplied by Evonik Goldschmidt
[c]known by the tradename STRUCTURE ZEA, supplied by Akzo Nobel
[d]known by the tradename SILSOFT A-1100, supplied by Momentive Performance Materials or KBE-903, supplied by Shinetsu
[e]known by the tradename SILSOFT 253, supplied by Momentive Performance Materials
[f]known by the tradename DOW CORNING CE-7114 SILICONE QUAT MICROEMULSION (previously known as XX-7113), supplied by Dow Corning
[g]known by the tradename GAFQUAT 755, supplied by ISP (Ashland)
[h]known by the tradename SALCARE SC 96, supplied by BASF Formulas above were prepared according to Table 1 and the following protocol.

Preparation of Side Kettle 1. 5% by weight of the total water was mixed with Polyquaternium-37 (and) Propylene glycol dicaprylate/Dicaprate (and) PPG-1 Trideceth-6 in a container.
2. In a separate container, 5% by weight of the total water was mixed with Aminopropyl Triethoxysilane and neutralized by lactic acid to a ph of about 4.
3. The Aminopropyl Triethoxysilane was then mixed with the Polyquaternium-37 (and) Propylene glycol dicaprylate/Dicaprate (and) PPG-1 Trideceth-6 solution.

Preparation of Main Kettle

1. Water was mixed with Polyquaternium-11 in a container.
2. Hydroxypropyl Starch Phosphate was added to the mixture. The batch was then heated to 70° C. and mixed for 30 minutes.

3. Fatty alcohol (e.g., Stearyl alcohol), behentrimonium chloride, and Quaternium-87 were added and stirred until the batch homogenized to form an emulsion.
4. The batch was cooled to 45° C. and fragrance was added.
5. The batch was then cooled to 30° C. Preservative and organic solvent were added to the batch.
6. The contents of the Side Kettle were added and mixed.
7. Silicone Microemulsion 1 or 2 and dyes, fragrance were added to the resulting final composition.

The inventive formulas prepared according to the above protocol were translucent.

Example 2: Testing on Hair

A panel of 12 women ranging from 18-55 years old from any ethnicity except African American tested inventive Conditioner Formula C containing Silicone Microemulsion 2 and inventive Conditioner Formula D containing Silicone Microemulsion 1. These women had self-perceived fine hair with medium to long, hair in length, and straight or wavy natural hair pattern. The women were users of mass volume shampoos several per week, with low conditioner usage 1 or less times per week due to heaviness and or weighing down of hair. The panelists were asked to use each inventive formula (C and D) after shampooing their hair using a shampoo provided for a minimum of 4 applications during a one week home usage. The women were asked to answer closed-ended questionnaire. The panelists noted their hair was visibly volumized, thicker, and had more movement and bounce versus their normal routine. In addition, the women indicated their hair was not weighed down and felt lightweight, versus their normal routine, wherein a conditioner was used 1 or less times a week due to heaviness and or weighing down of hair.

Example 3: Conditioner Commercial Formula

TABLE 2

Comparative Commercial Conditioner Formula Y
(advertised for its volumizing properties)

INCI US

Water
Cetyl Alcohol
Steramidopropyl Dimethylamine
Stearyl Alcohol
Quaternium 18
Fragrance
Bis Aminopropyl Dimethicone
Benzyl Alcohol
Cetearyl Alcohol
Hydroxypropyl Guar
Glyceryl Stearate
Panthenyl Ethyl Ether
Oleyl Alcohol
Trisodium Ethylenediamine
Methylchloroisothiazolinone
Methylsothiazolinone The performance/effect of the inventive conditioner on hair was evaluated in a shampoo-conditioner regimen and compared with the performance of a shampoo-conditioner regimen using the comparative commercial conditioner product above. Conditioner Formula E from Table 1 was tested. The shampoos used in the shampoo-conditioner regimens mainly comprise anionic sulfate surfactants and amphoteric surfactants.

Example 4: Mannequin Test

A half head test was performed on a mannequin head for visual volume and tactile attributes. On the left side of the head, the hair was shampooed and then treated with inventive Conditioner Formula A. On the right side of the head, the hair was shampooed and then treated Comparative Commercial Conditioner Y.

The mannequin's hair exhibited visibly more volume and root lift as well as better styling on the left side where the inventive Conditioner Formula was applied as compared to the hair on the right side. See FIG. 1.

Example 5: Salon Test I

The inventive conditioner containing Silicone Microemulsion 2 (Formula E) was tested on the hair of the heads of 8 human panelists in a salon. Attributes of the hair after being treated with the bundles are graded on a scale of 1-5, 1 being the lowest and 5 being the greatest. A p-value is then determined from the grading, and therefore its degree of statistical significance. A low p-value indicates that there is a low variability in the data. The degree of statistical significance is indicated by the number of stars. The greater the number of stars, the greater the degree of statistical significance. In general, a higher grade indicates better performance or cosmetic attribute; however, for the attribute of "weight", a lower grade indicates lighter weight of product on the hair, a more desirable attribute.

TABLE 3

Salon Test - Shampoo plus Inventive Conditioner
Formula E versus Shampoo plus Conditioner Y

| Attribute | Shampoo and Conditioner Formula E | Shampoo and Comparative Conditioner Formula | P-Value | Degree of Statistical Significance |
|---|---|---|---|---|
| Volume (wet volume) | 1.69 | 1.31 | 0.1970 | * |
| Bounce | 2.25 | 1.56 | 0.0732 | ** |
| Mass Effect of wet Hair | 2.38 | 1.75 | 0.1064 | * |
| Weight (wet) | 1.06 | 2.13 | 0.0571 | ** |
| Volume (dry volume) | 2.56 | 2.19 | 0.3358 | NS |
| Mass Effect of Hair (dry) | 2.69 | 1.94 | 0.0404 | *** |
| Body | 2.63 | 2.06 | 0.0938 | ** |
| Discipline | 3.13 | 2.31 | 0.0417 | *** |
| Providing Shape | 2.88 | 2.25 | 0.1176 | * |
| Smoothness (visual) | 3.31 | 2.50 | 0.0034 | *** |
| Smoothness (feel) | 3.13 | 2.88 | 0.1705 | * |
| Weight (dry) | 1.25 | 1.13 | 0.7980 | NS |

While it was observed that the detangling effect observed using the inventive conditioner formula was lower, statistically significantly better final results (on dry hair) were obtained using the shampoo-inventive conditioner bundle as compared to the shampoo-comparative commercial conditioner bundle with respect to mass effect of wet hair, body, bounce, weight (less weight observed), discipline, smoothness (visual), smoothness (feel), ease of passing fingers, providing shape, and volume. Also, comparable results were obtained using the shampoo-inventive conditioner bundle with respect to the other attributes which indicate that the inventive conditioner performed just as well as the commercial comparative conditioner (benchmark). In addition, the inventive conditioner had a translucent appearance while the commercial comparative conditioner was opaque.

Example 6: Salon Test II

The inventive conditioner Formula F containing Silicone Microemulsion 1 was tested on the hair of the heads of 8 human panelists in a salon. Attributes of the hair after being treated with the bundles are graded on a scale of 1-5, 1 being the lowest and 5 being the greatest. A p-value is then determined from the grading, and therefore its degree of statistical significance. A low p-value indicates that there is a low variability in the data. The degree of statistical significance is indicated by the number of stars. The greater the number of stars, the greater the degree of statistical significance. In general, a higher grade indicates better performance or cosmetic attribute; however, for the attribute of "weight", a lower grade indicates lighter weight of product on the hair, a more desirable attribute.

TABLE 4

Salon Test - Shampoo plus Inventive Conditioner Formula F versus Shampoo plus Conditioner Y

| Attribute | Shampoo and Conditioner Formula E | Shampoo and Comparative Commercial Conditioner Formula | P-Value | Degree of Significance |
|---|---|---|---|---|
| Volume (wet) | 1.06 | 1.44 | 0.0796 | ** |
| Bounce | 2.19 | 1.81 | 0.3358 | NS |
| Mass Effect of Wet Hair | 2.31 | 1.56 | 0.0025 | *** |
| Weight (wet) | 1.50 | 1.69 | 0.7231 | NS |
| Volume (dry) | 2.38 | 2.13 | 0.5527 | NS |
| Mass Effect | 2.13 | 1.88 | 0.3506 | NS |
| Body | 2.13 | 1.75 | 0.2654 | NS |
| Discipline | 3.19 | 2.69 | 0.2275 | NS |
| Providing Shape | 2.69 | 1.94 | 0.0636 | ** |
| Smoothness (visual) | 2.94 | 2.75 | 0.5040 | NS |
| Smoothness (feel) | 2.38 | 2.63 | 0.4700 | NS |
| Weight (dry) | 1.06 | 1.69 | 0.1287 | * |

It was observed that the shampoo-inventive conditioner bundle performed comparably to the shampoo-comparative commercial conditioner bundle. From the Table above, comparable results between the use of the shampoo-inventive conditioner bundle and the shampoo-comparative commercial conditioner bundle were obtained with respect to most of the attributes which indicate that the inventive conditioner performed just as well as the commercial comparative conditioner (benchmark). For the attribute of light weight and providing shape, the shampoo-inventive conditioner bundle performed statistically significantly better than the commercial comparative bundle. It was also observed from the salon test that the detangling effects from the invention were comparable to those provided by the benchmark.

In addition, the inventive conditioner had a translucent appearance while the commercial comparative conditioner was opaque.

It is to be understood that the foregoing describes preferred embodiments of the disclosure and that modifications may be made therein without departing from the spirit or scope of the disclosure as set forth in the claims.

What is claimed is:

1. A translucent rinse-out volumizing hair conditioning composition comprising:
   (a) a cationic agent comprising:
      (i) from about 1% to about 2% by weight of behentrimonium chloride; and
      (ii) from about 3% to about 4% by weight of quaternium-87;
   (b) from about 4% to about 6.5% by weight of hydroxypropyl starch phosphate;
   (c) from about 0.4% to about 0.8% by weight of 3-aminopropyltriethoxysilane;
   (d) from about 0.2% to about 0.9% by weight of amodimethicone;
   (e) from about 0.05% to about 0.8% by weight of polyquaternium-11; and
   (f) water;
   wherein all weights are based on the total weight of the composition; and
   wherein the composition is substantially free of fatty alcohols.

2. The composition according to claim 1, wherein the amodimethicone is in the form of an emulsion comprising at least one surfactant selected from nonionic surfactants, cationic surfactants, or mixtures thereof.

3. The composition according to claim 2, wherein the emulsion is a microemulsion.

4. A method for conditioning hair, the method comprising contacting the hair with a conditioning composition of claim 1.

5. The method according to claim 4, further comprising leaving the conditioning composition on the hair for a leave-on time and then rinsing the hair with water.

6. The conditioning composition according to claim 1, further comprising at least one organic solvent.

7. The conditioning composition according to claim 1, further comprising at least one surfactant selected from nonionic surfactants, cationic surfactants, or mixtures thereof.

8. The conditioning composition according to claim 1, further comprising at least one additional cationic agent other than (a)(i) or (a)(ii).

9. The conditioning composition according to claim 8, wherein the at least one additional cationic agent is chosen from cetrimonium chloride, behentrimonium methosulfate, quaternium-83, or mixtures thereof.

10. The conditioning composition according to claim 1, further comprising at least one additional silane other than (c) or (d).

11. The conditioning composition according to claim 10, wherein the at least one additional silane is silicone quaternium-16.

12. The conditioning composition according to claim 10, wherein the at least one additional silane is chosen from amino silicones.

13. The conditioning composition according to claim 1, wherein the pH of the composition ranges from about 3 to about 7.

14. The conditioning composition according to claim 1, further comprising at least one additive chosen from rheology modifiers, thickeners, surfactants, nacreous agents, dyes, pigments, fragrances, mineral oils, plant oils, synthetic oils, waxes, vitamins, proteins, vitamins, UV-screening agents, free-radical scavengers, antidandruff agents, hair-loss counteractants, hair restorers, preserving agents, pH stabilizers, solvents, or mixtures thereof.

* * * * *